United States Patent [19]

Baus et al.

[11] Patent Number: 4,945,167
[45] Date of Patent: Jul. 31, 1990

[54] PREPARATION OF N-HYDROXYPYRAZOLES

[75] Inventors: Ulf Baus, Dossenheim; Wolfgang Reuther; Erwin Hahn, both of Heidelberg, all of Fed. Rep. of Germany

[73] Assignee: Basf Aktiengesellschaft, Ludwigshafen, Fed. Rep. of Germany

[21] Appl. No.: 367,047

[22] Filed: Jun. 16, 1989

[30] Foreign Application Priority Data

Jun. 18, 1988 [DE] Fed. Rep. of Germany ....... 3820739

[51] Int. Cl.$^5$ ........................................... C07D 231/12
[52] U.S. Cl. ..................................... 548/375; 548/376
[58] Field of Search ............... 548/369, 371, 372, 375, 548/376

[56] References Cited

U.S. PATENT DOCUMENTS 4,350,819 9/1982 Rieber et al. ..................... 548/375

*Primary Examiner*—Robert W. Ramsuer
*Attorney, Agent, or Firm*—Oblon, Spivak, McClelland, Maier & Neustadt

[57] ABSTRACT

N-hydroxypyrazoles of the general formula I

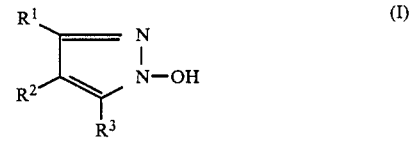

where $R^1$, $R^2$ and $R^3$ may be identical or different and are each hydrogen or halogen, are prepared by a process in which a pyrazole of the general formula II

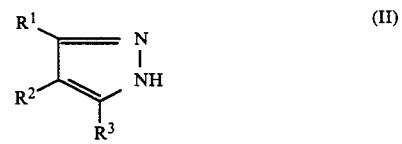

where $R^1$, $R^2$ and $R^3$ have the meanings stated for formula I, is reacted with an aliphatic or aromatic peroxocarboxylic acid, preferably in the presence of from 0 to 15 moles of an alkali metal hydroxide, alkaline earth metal hydroxide, alkali meteal carbonate or alkaline earth metal carbonate in such a way that the reaction temperature is from $-5°$ C. to 60°C.

The reaction can be carried out in water as a solvent or in a 2-phase system consisting of water and an inert organic solvent which is poorly miscible with water, in the presence or absence of a suitable phase transfer catalyst. The peroxocarboxylic acid can be prepared in the reaction mixture before the reaction from $H_2O_2$ and an acyl halide or a carboxylic anhydride or can be used in the form of an alkali metal salt or alkaline earth metal salt.

12 Claims, No Drawings

PREPARATION OF N-HYDROXYPYRAZOLES

The present invention relates to the preparation of N-hydroxypyrazole and its derivatives from the corresponding pyrazoles.

N-hydroxypyrazole and its derivatives are important intermediates for the preparation of substances having a broad biological action spectrum. For example, DE No. 3 409 317 describes the preparation of useful nitrification inhibitors for ammonium nitrogen from N-hydroxypyrazoles. Furthermore, DE No. 35 32 880 describes the preparation of 1,4-disubstituted derivatives of N-hydroxypyrazole as compounds having a selective action on histamine $H_2$ receptors. There has therefore been no lack of attempts to find an advantageous process for the preparation of N-hydroxypyrazoles.

According to German Laid-Open Application DOS No. 3,031,385, N-hydroxypyrazole is prepared by a multistage synthesis from the building blocks azodicarboxylate, cyclopentadiene, nitrile oxide and a peroxide. The disadvantages of this process are the multistage procedure, the low yield and the fact that the N-hydroxypyrazole is obtained as a mixture with isoxazoles.

N-hydroxypyrazoles substituted in the nucleus can be prepared, for example, according to J. Org. Chem. 34 (1969), 187-194, by nitrozation of correspondingly substituted $\alpha,\beta$-unsaturated oximes followed by reduction of the 3,4-diazacyclopentadienone dioxides obtained. The disadvantages of this process are the multistage procedure and the fact that only N-hydroxypyrazoles substituted in the nucleus can be prepared.

It is an object of the present invention to provide a simple and economical process which permits the preparation of both N-hydroxypyrazole itself and N-hydroxypyrazoles substituted in the nucleus.

We have found that this object is achieved and that, surprisingly, N-hydroxypyrazole itself and N-hydroxypyrazoles substituted in the nucleus can be obtained in a simple manner if the corresponding pyrazoles are reacted with a peroxocarboxylic acid.

Although it was known that hydroxylamines can be prepared in the reaction of primary or secondary aliphatic amines with hydrogen peroxide or its acyl derivatives, such as dibenzoyl peroxide, in combination with catalysts and subsequent hydrolysis of the resulting O-benzoyl-N-hydroxylamines (cf. Houben-Weyl, Methoden der organischen Chemie, Vol. 10/1, Thieme-Verlag, 1971, pages 1135-1137), this reaction is expressly restricted to aliphatic amines (loc. cit.).

The present invention accordingly relates to a process for the preparation of N-hydroxypyrazoles of the general formula I

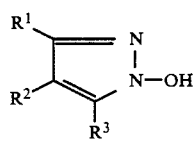

where $R^1$, $R^2$ and $R^3$ may be identical or different and are each hydrogen or halogen, wherein a pyrazole of the general formula II

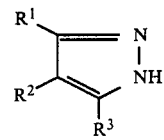

where $R^1$, $R^2$ and $R^3$ have the meanings stated for formula I, is reacted with an aliphatic or aromatic peroxocarboxylic acid in such a way that the reaction temperature is from $-5°$ C. to $60°$ C.

Particularly good yields are obtained in this reaction if it is carried out in the presence of from 1 to 15 moles of an alkali metal hydroxide, alkaline earth metal hydroxide, alkali metal carbonate or alkaline earth metal carbonate, preferably in the presence of from 1.5 to 9 moles of an alkali metal hydroxide per mole of the pyrazole. It may be advantageous if, before being reacted with the peroxocarboxylic acid, the pyrazole of the formula II is converted in a conventional manner with an alkali metal hydroxide, alkali metal hydride or alkali metal carbonate into one of its metal salts of the general formula III

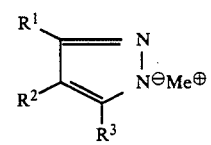

where $R^1$, $R^2$ and $R^3$ have the meanings stated for formula I and Me$^\oplus$ is a cation of an alkali metal.

Suitable pyrazoles of the general formula II are pyrazole, 3-chloropyrazole, 4-chloropyrazole, 3-bromopyrazole, 4-bromopyrazole, 3-iodopyrazole, 4-iodopyrazole, 3,4-dichloropyrazole, 3,4,5-trichloropyrazole, 3,4-dibromopyrazole, 3,4,5-tribromopyrazole, 3,4-diiodopyrazole and 3,4,5-triiodopyrazole.

The pyrazoles are converted into their metal salts of the general formula III in a conventional manner by reacting the pyrazoles in water or in an inert solvent with an alkali metal hydroxide or alkali metal hydride or alkali metal carbonate at from 0° to 60° C.

Suitable peroxocarboxylic acids are both aromatic peroxocarboxylic acids, such as m-chloroperbenzoic acid, perbenzoic acid, monoperphthalic acid, etc., and aliphatic peroxocarboxylic acids, such as peracetic acid, perpropionic acid, trifluoroperacetic acid, monopersuccinic acid, etc. Monoperphthalic acid is particularly advantageously used.

The stoichiometric ratio of pyrazole II and peroxo acid is in general from 1:1 to 1:2.

The reaction is generally carried out in a solvent. Examples of solvents for this reaction are aliphatic ethers, such as diethyl ether, diisopropyl ether or diethylene glycol dimethyl ether, cyclic ethers, such as tetrahydrofuran (THF) or dioxane, and aromatic hydrocarbons, such as toluene, and halohydrocarbons, such as methylene chloride, chloroform or chlorobenzene.

In many cases, water is particularly advantageously used as the solvent. When peroxocarboxylic acids which are sensitive to hydrolysis are used, a 2-phase system consisting of water and a solvent which is water-immiscible or poorly miscible with water can advantageously be employed. Suitable solvents here are essentially aliphatic and aromatic hydrocarbons and chlorohydrocarbons. Particular examples are cyclohexane, toluene and methylene chloride. When a suitable 2-phase system is employed, it is advisable to carry out the reaction in the presence of a suitable phase transfer catalyst.

A large number of phase transfer catalysts are suitable for the novel process (for a general overview, see V. Dehmlow, Angew. Chem. 89 (1977), 521–533). Particularly preferred phase transfer catalysts are:

1. Tetraalkylammonium salts of the general formula IV

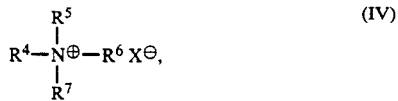

where $R^4$, $R^5$, $R^6$ and $R^7$ may be identical or different and are each alkyl of 1 to 22 carbon atoms or alkyl of not more than 25 carbon atoms which contains functional groups, such as hydroxyl, carboxamide or ether groups, e.g. methyl, ethyl, propyl, isopropyl, butyl, octyl, dodecyl, $C_{16}H_{33}$, hydroxy(iso)propyl or

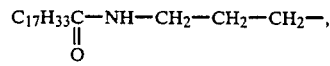

or are each phenyl or phenyl-substituted alkyl (e.g. benzyl) of not more than 20 carbon atoms and $X^\ominus$ is an anion of an acid, such as $I^-$, $Cl^-$, $Br^-$, $(HSO_4)^-$, $(CN)^-$, $(BF_4)^-$ or $OH^-$; in particular the very economical trimethylbenzylammonium chloride, which can be used in the form of its 50% strength aqueous solution, and tricaprylmethylammonium chloride; and 2. tetraalkylphosphonium salts of the general formula V

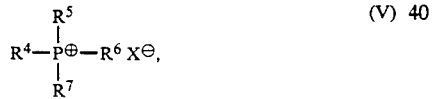

where $R^4$, $R^5$, $R^6$, $R^7$ and $X^\ominus$ have the meanings stated for the formula (IV); in particular tri-n-octylmethylphosphonium iodide.

Mixtures of the abovementioned phase transfer catalysts and supported phase transfer catalysts are also suitable.

The phase transfer catalysts are used for the novel process in amounts of from 0.1 to 1, preferably from 0.3 to 0.5, mole per mole of pyrazole.

Depending on the reactivity of the peroxocarboxylic acid used, the reaction begins at as low as below 0° C., but in most cases only at about 20° C.

The reaction takes place particularly smoothly in the presence of a relatively large amount of a base, such as an alkali metal hydroxide, alkaline earth metal hydroxide, alkali metal carbonate or alkaline earth metal carbonate. In general, 1 equivalent of the base is preferably added to the reaction mixture before the addition of the peroxocarboxylic acid. However, instead of the peroxocarboxylic acid, it is also possible to use one of its metal salts, in particular an alkali metal salt or alkaline earth metal salt of the peroxocarboxylic acid.

It is also possible to prepare the peroxocarboxylic acid in a conventional manner in the reaction mixture before the reaction. For this purpose, hydrogen peroxide is reacted with, for example, an acyl halide, in particular an acyl chloride, or a carboxylic anhydride. In this case too, it is advisable to employ a 2-phase system when using hydrolysis-sensitive peroxocarboxylic acids or acyl halides or carboxylic anhydrides.

In a particularly preferred procedure, the pyrazole is dissolved in about a 9-fold molar excess of a roughly 50% strength by weight aqueous potassium hydroxide solution, the solution is cooled to about 0° C., a little more than the equimolar amount of a concentrated aqueous $H_2O_2$ solution is slowly added and the acyl halide or carboxylic anhydride is then introduced a little at a time and the reaction mixture is heated to about 20° C.

In general, it is advisable to allow the stirred reaction mixture to continue reacting for some time at room temperature and finally to heat it again briefly to about 80° C. to decompose any excess $H_2O_2$ or peroxocarboxylic acid still present.

The reaction mixture is worked up in a conventional manner. For example, the cooled reaction mixture is acidified with an acid, such as sulfuric acid, and the reaction product is extracted with a suitable solvent, for example ethyl acetate. Removal of the solvent gives an oil, from which the desired N-hydroxypyrazole crystallizes. The latter can be purified, for example, by crystallization from cyclohexane.

With the aid of the novel process, the N-hydroxypyrazoles of the formula I which are desirable as useful intermediates for many active ingredients, can be prepared in a very simple and advantageous manner in relatively good yields.

The Examples which follow illustrate the novel process.

EXAMPLE 1

0.4 mole of pyrazole was dissolved in 192 g (1.5 moles) of a 50% strength by weight aqueous KOH. The stirred solution was cooled to 0° C., and 34 g (0.5 mole) of a 50% strength by weight aqueous hydrogen peroxide solution were slowly added. Thereafter, 0.5 mole of the carboxylic anhydride stated in the Table below was added a little at a time and the reaction mixture was then heated to 20° C. Stirring was continued for several hours and the reaction mixture was heated briefly to 80° C. to decompose the peroxide and cooled again to room temperature. It was then acidified with sulfuric acid, the precipitated potassium sulfate was filtered off and the filtrate was extracted 3 times with ethyl acetate. The organic phases were dried and the solvent was removed to give a pale yellow oil, from which the N-hydroxypyrazole crystallized. The N-hydroxypyrazole obtained was crystallized from cyclohexane. The following experiments were carried out:

| Carboxylic anhydride | Pyrazole | | | Yield |
| --- | --- | --- | --- | --- |
| | $R^1$ | $R^2$ | $R^3$ | [g/% of theory] |
| Succinic anhydride | H | H | H | 6.7 g/20% |
| Phthalic anhydride | H | H | H | 23.4 g/70% |
| Phthalic anhydride | H | Cl | H | 32 g/68% |

EXAMPLE 2

35.3 g (0.5 mole) of pyrazole were dissolved in 250 ml of toluene and 73 g (0.65 mole) of a 50% strength by weight potassium hydroxide solution. 0.25 g of benzyltriethylammonium chloride was added, after which the mixture was cooled to 0° C. Thereafter, 11.33 g (0.166 mole) of a 50% strength aqueous hydrogen peroxide solution was slowly added dropwise, followed by the slow dropwise addition of 23.4 g (0.166 mole) of benzoyl chloride. The reaction mixture was then allowed to warm up slowly to 20° C. and was stirred for several hours. To work up the mixture, the aqueous phase was separated off and acidified with sulfuric acid, benzoic acid being precipitated. After the precipitate had been filtered off, the aqueous phase was extracted by shaking with ethyl acetate and the organic phase was separated off and dried. Removal of the solvent gave an oil, from which 6.0 g (71.4 millimoles) of N-hydroxypyrazole could be isolated.

Yield: 43% of theory, based on $H_2O_2$ used.

When propionic anhydride was used instead of benzoyl chloride, the yield was 23% of theory.

EXAMPLE 3

5.1 g (0.075 mole) of pyrazole were dissolved in a mixture of 25 ml of water and 25 ml of acetone. 23.6 g (0.075 mole) of m-chloroperbenzoic acid (55% strength) were added at room temperature and the mixture was stirred. After 3 days, it was worked up similarly to Example 1.

Yield: 2.1 g of N-hydroxypyrazole, corresponding to 30% of theory.

EXAMPLE 4

25.65 g (0.3 mole) of 4-chloropyrazole were suspended in 300 g of water, after which 89.6 g (0.8 mole) of a 50% strength aqueous KOH solution were added. The mixture was stirred at room temperature, after which 74.4 g (0.15 mole) of magnesium-bis-(2-carboxylato-monoperoxybenzoic acid) hexahydrate (Peroxid-Chemie GmbH) were added a little at a time. The mixture was stirred for two days at room temperature and then worked up similarly to Example 1.

Yield: 14.4 g (0.12 mole) of 4-chloro-N-hydroxypyrazole, corresponding to 40% of theory.

EXAMPLE 5

7.65 g (0.075 mole) of 4-chloropyrazole were suspended in 100 ml of water and the suspension obtained first had added to it 72 g (0.64 mole) of a 50% strength aqueous KOH solution and then at 0° C. 17 g (0.15 mole) of a 30% strength aqueous hydrogen peroxide solution.

After the reaction mixture had been stirred for 5 minutes, 28 g (0.18 mole) of phthalic anhydride were added in small portions at 10° C., and the whole was stirred overnight and then worked up similarly to Example 1.

Yield: 7.1 g of 4-chloro-N-hydroxypyrazole, corresponding to 80% of theory.

We claim:
1. A process for the preparation of a N-hydroxypyrazole of the formula I

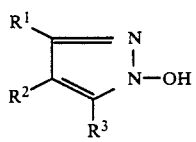

(I)

where $R^1$, $R^2$ and $R^3$ may be identical or different and are each hydrogen or halogen, wherein a pyrazole of the formula II

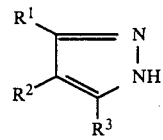

(II)

where $R^1$, $R^2$ and $R^3$ have the meanings stated for formula I, is reacted with an aliphatic or aromatic peroxocarboxylic acid in such a way that the reaction temperature is from −5° C. to 60° C.

2. A process for the preparation of an N-hydroxypyrazole of the formula I as claimed in claim 1, wherein the reaction is carried out in the presence of from 1 to 15 moles of an alkali metal hydroxide, alkaline earth metal hydroxide, alkali metal carbonate or alkaline earth metal carbonate.

3. A process for the preparation of an N-hydroxypyrazole of the formula I as claimed in claim 1, wherein the reaction is carried out using the peroxocarboxylic acid in the presence of from 1.5 to 4 moles of an alkali metal hydroxide.

4. A process for the preparation of an N-hydroxypyrazole of the formula I as claimed in claim 1, wherein, before being reacted with the peroxocarboxylic acid, the pyrazole of the formula II is converted in a conventional manner with an alkali metal hydroxide, alkali metal hydride or alkali metal carbonate into one of its metal salts of the formula III

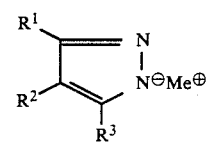

(III)

where $R^1$, $R^2$ and $R^3$ have the meanings stated for formula I and $Me^\oplus$ is a cation of an alkali metal.

5. A process for the preparation of an N-hydroxypyrazole of the formula I as claimed in claim 1, wherein the peroxocarboxylic acid is prepared in a conventional manner in the reaction mixture before the reaction from hydrogen peroxide and an acyl halide or carboxylic anhydride.

6. A process for the preparation of an N-hydroxypyrazole of the formula I as claimed in claim 1, wherein the aromatic peroxocarboxylic acid used is m-chloroperbenzoic acid, perbenzoic acid or monophthalic acid.

7. A process for the preparation of an N-hydroxypyrazole of the formula I as claimed in claim 1, wherein the aliphatic peroxocarboxylic acid used is peracetic acid, perpropionic acid, trifluoroperacetic acid or monopersuccinic acid.

8. A process for the preparation of an N-hydroxypyrazole of the formula I as claimed in claim 1, wherein the reaction is carried out in water as the solvent.

9. A process for the preparation of an N-hydroxypyrazole of the formula I as claimed in claim 1, wherein the reaction is carried out in a 2-phase system consisting of water and an inert organic solvent which is water-immiscible or poorly miscible with water.

10. A process for the preparation of an N-hydroxypyrazole of the formula I as claimed in claim 9, wherein the reaction is carried out in the presence of a phase transfer catalyst.

11. A process for the preparation of an N-hydroxypyrazole of the formula I as claimed in claim 10, wherein the phase transfer catalyst used is a tetraalkylammonium salt of the formula IV

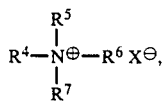 (IV)

where $R^4$, $R^5$, $R^6$ and $R^7$ may be identical or different and are each alkyl of 1 to 22 carbon atoms or alkyl of not more than 25 carbon atoms which contains functional groups, such as hydroxyl, carboxamide or ether groups, e.g. methyl, ethyl, propyl, isopropyl, butyl, octyl, dodecyl, $C_{16}H_{33}$, hydroxy(iso)propyl or

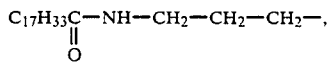

or are each phenyl or phenyl-substituted alkyl (e.g. benzyl) of not more than 20 carbon atoms and $X^\ominus$ is an anion of an acid, such as $I^-$, $Cl^-$, $Br^-$, $(HSO_4)^-$, $(CN)^-$, $(BF_4)^-$ or $OH^-$.

12. A process for the preparation of an N-hydroxypyrazole of the formula I as claimed in claim 1, wherein an alkali metal salt or alkaline earth metal salt of a peroxocarboxylic acid is used instead of a peroxocarboxylic acid.

* * * * *